United States Patent
Chen et al.

(10) Patent No.: US 9,970,053 B2
(45) Date of Patent: May 15, 2018

(54) WASHING-FREE TEMPLATE-READY PCR DETECTION METHOD FOR RNA

(71) Applicant: ZHEJIANG JFK BIOLOGICAL TECHNOLOGY CO. LTD., Hangzhou (CN)

(72) Inventors: Ran Chen, Zhejiang (CN); Xiaozheng Jin, Zhejiang (CN)

(73) Assignee: ZHEJIANG JFK BIOLOGICAL TECHNOLOGY CO. LTD., Hangzhou, Zhejiang (CN)

(*) Notice: Subject to any disclaimer, the term of this patent is extended or adjusted under 35 U.S.C. 154(b) by 223 days.

(21) Appl. No.: 14/953,167

(22) Filed: Nov. 27, 2015

(65) Prior Publication Data

US 2016/0160266 A1    Jun. 9, 2016

Related U.S. Application Data

(63) Continuation of application No. PCT/CN2014/078530, filed on May 27, 2014.

(30) Foreign Application Priority Data

May 28, 2013    (CN) .......................... 2013 1 0205271

(51) Int. Cl.
*C12Q 1/68*    (2006.01)
*C12P 19/34*    (2006.01)

(52) U.S. Cl.
CPC .......... *C12Q 1/686* (2013.01); *C12Q 1/6848* (2013.01)

(58) Field of Classification Search
CPC ................. C12Q 1/6848; C12Q 1/686; C12Q 2525/137; C12Q 2547/101; C12Q 2565/537
See application file for complete search history.

(56) References Cited

U.S. PATENT DOCUMENTS

2004/0185443 A1* 9/2004 Dahl .................... C12Q 1/6816
                                                       435/6.1

FOREIGN PATENT DOCUMENTS

| CN | 1311334 | 9/2001 |
|---|---|---|
| CN | 102851387 | 1/2013 |
| CN | 102864233 | 1/2013 |
| CN | 103333954 | 10/2013 |

OTHER PUBLICATIONS

International Search Report for PCT/CN2014/078530, dated Sep. 3, 2014, and English language translation thereof, 4 pages total.

* cited by examiner

*Primary Examiner* — Young J Kim
(74) *Attorney, Agent, or Firm* — Hamre, Schumann, Mueller & Larson, P.C.

(57) ABSTRACT

Provided in the present invention is a washing-free template-ready PCR detection method for RNA. On the basis of retaining the advantages of the original template-ready PCR method, i.e., there being no need to purify and extract the RNA, no need for a reverse transcription reaction, etc., the method of the present invention designs a probe for the restriction enzymes to thereby integrate the enzyme digestion reaction, so as to eliminate the interference of various pollution sources of double-stranded DNA with no need for a washing step.

4 Claims, 1 Drawing Sheet

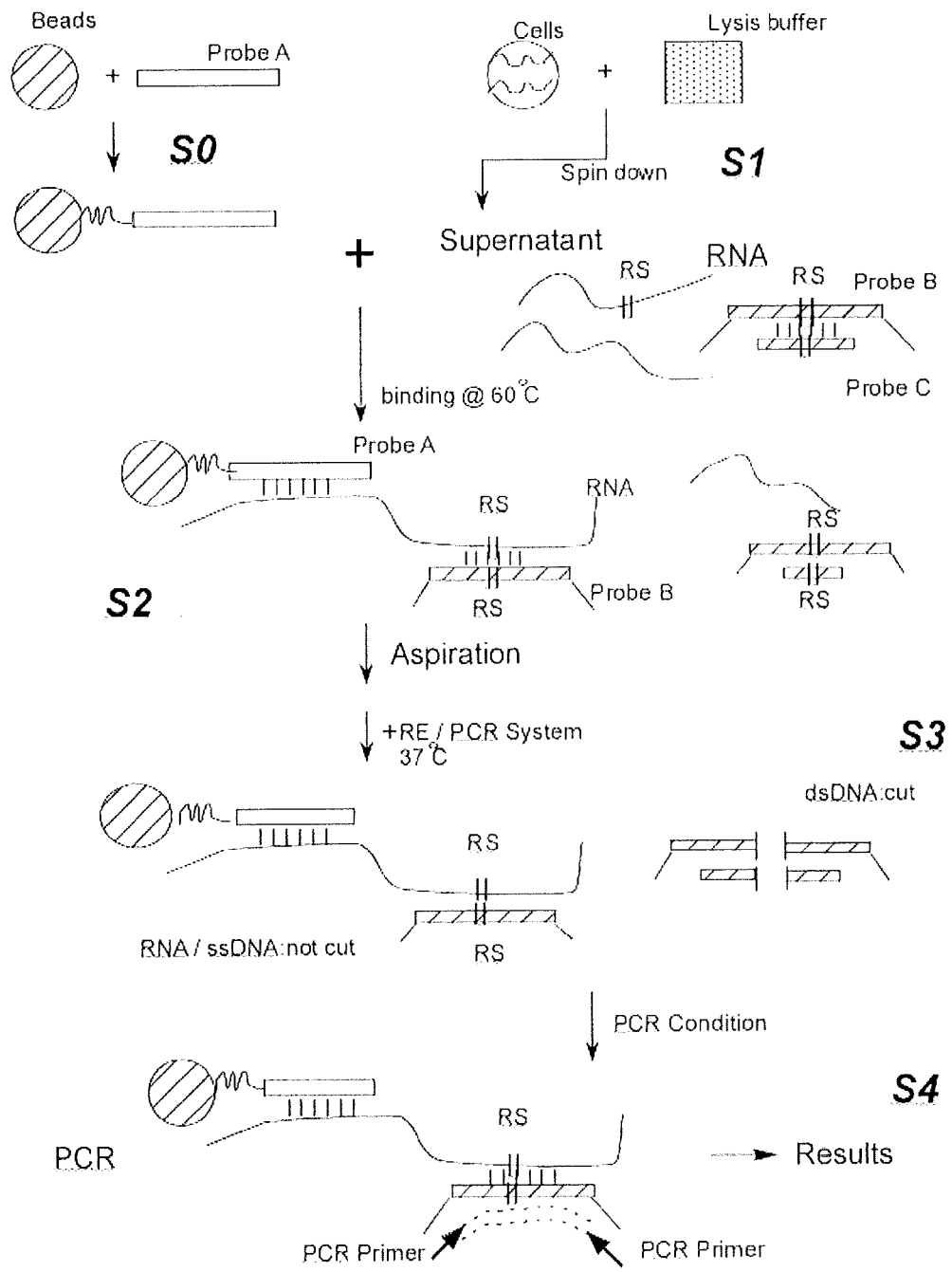

SEQUENCE LISTING

```
<160> NUMBER OF SEQ ID NOS: 52

<210> SEQ ID NO 1
<211> LENGTH: 22
<212> TYPE: DNA
<213> ORGANISM: Artificial Sequence
<220> FEATURE:
<223> OTHER INFORMATION: universal PCR primer

<400> SEQUENCE: 1
gactgactcc tggcatcctc gg                                          22

<210> SEQ ID NO 2
<211> LENGTH: 22
<212> TYPE: DNA
<213> ORGANISM: Artificial Sequence
<220> FEATURE:
<223> OTHER INFORMATION: universal PCR primer

<400> SEQUENCE: 2
ccttctctgg acctgcgacg ac                                          22

<210> SEQ ID NO 3
<211> LENGTH: 44
<212> TYPE: DNA
<213> ORGANISM: Artificial Sequence
<220> FEATURE:
<223> OTHER INFORMATION: anchor probe A  for human DKK1

<400> SEQUENCE: 3
ccgttcttgt agaacacaca catacgtaca cacacaaa cctc                    44

<210> SEQ ID NO 4
<211> LENGTH: 79
<212> TYPE: DNA
<213> ORGANISM: Artificial Sequence
<220> FEATURE:
<223> OTHER INFORMATION: template probe B for human DKK1

<400> SEQUENCE: 4
gactgactcc tggcatcctc ggcgcttcct gcaggcgaga cagatttgca cgcctgcgtc  60
gtcgcaggtc cagagaagg                                              79

<210> SEQ ID NO 5
<211> LENGTH: 16
<212> TYPE: DNA
<213> ORGANISM: Artificial Sequence
<220> FEATURE:
<223> OTHER INFORMATION: complementary probe C for human DKK1
```

```
<400> SEQUENCE: 5
tcgcctgcag gaagcg                                                         16

<210> SEQ ID NO 6
<211> LENGTH: 40
<212> TYPE: DNA
<213> ORGANISM: Artificial Sequence
<220> FEATURE:
<223> OTHER INFORMATION: anchor probe A for human TLR2

<400> SEQUENCE: 6
gttggccctc tatatccatg ggttctgcat ccatgaagtc                                40

<210> SEQ ID NO 7
<211> LENGTH: 83
<212> TYPE: DNA
<213> ORGANISM: Artificial Sequence
<220> FEATURE:
<223> OTHER INFORMATION: template probe B for human TLR2

<400> SEQUENCE: 7
ccttctctgg acctgcgacg actatgaatt ttgatatcca cgaggatcct gcaaccaatt          60
cccgaggatg ccaggagtca gtc                                                 83

<210> SEQ ID NO 8
<211> LENGTH: 19
<212> TYPE: DNA
<213> ORGANISM: Artificial Sequence
<220> FEATURE:
<223> OTHER INFORMATION: complementary probe C for human TLR2

<400> SEQUENCE: 8
gttgcaggat cctcgtgga                                                      19

<210> SEQ ID NO 9
<211> LENGTH: 36
<212> TYPE: DNA
<213> ORGANISM: Artificial Sequence
<220> FEATURE:
<223> OTHER INFORMATION: anchor probe A for human TLR7

<400> SEQUENCE: 9
ccatcttggg ggcacatgct gaagagagtt actgtg                                   36

<210> SEQ ID NO 10
<211> LENGTH: 89
<212> TYPE: DNA
<213> ORGANISM: Artificial Sequence
<220> FEATURE:
<223> OTHER INFORMATION: template probe B for human TLR7

<400> SEQUENCE: 10
gactgactcc tggcatcctc ggtgatttcc tctgaattcc agagttctaa gagactcact          60
ctccatggtc gtcgcaggtc cagagaagg                                           89

<210> SEQ ID NO 11
<211> LENGTH: 22
<212> TYPE: DNA
<213> ORGANISM: Artificial Sequence
<220> FEATURE:
<223> OTHER INFORMATION: complementary probe C for human TLR7

<400> SEQUENCE: 11
aactctggaa ttcagaggaa at                                                  22
```

<210> SEQ ID NO 12
<211> LENGTH: 36
<212> TYPE: DNA
<213> ORGANISM: Artificial Sequence
<220> FEATURE:
<223> OTHER INFORMATION: anchor probe A for human XRCC6

<400> SEQUENCE: 12
ccagcgactc ctctgggtac acgaacaggg agggcc                          36

<210> SEQ ID NO 13
<211> LENGTH: 81
<212> TYPE: DNA
<213> ORGANISM: Artificial Sequence
<220> FEATURE:
<223> OTHER INFORMATION: template probe B for human XRCC6

<400> SEQUENCE: 13
ccttctctgg acctgcgacg actggtcaag ctctagaatt cgttttgcac ctggattatc    60
cgaggatgcc aggagtcagt c                                             81

<210> SEQ ID NO 14
<211> LENGTH: 21
<212> TYPE: DNA
<213> ORGANISM: Artificial Sequence
<220> FEATURE:
<223> OTHER INFORMATION: complementary probe C for human XRCC6

<400> SEQUENCE: 14
gcaaaacgaa ttctagagct t                                             21

<210> SEQ ID NO 15
<211> LENGTH: 30
<212> TYPE: DNA
<213> ORGANISM: Artificial Sequence
<220> FEATURE:
<223> OTHER INFORMATION: anchor probe A for hTERT

<400> SEQUENCE: 15
ggtgcgggcc tgggtgtggg ccgcccctcc                                    30

<210> SEQ ID NO 16
<211> LENGTH: 76
<212> TYPE: DNA
<213> ORGANISM: Artificial Sequence
<220> FEATURE:
<223> OTHER INFORMATION: template probe B for hTERT

<400> SEQUENCE: 16
gactgactcc tggcatcctc ggatggagcc ctgcgggatc cctggcact ggacgtcgtc     60 gcaggtccag agaagg                                                   76

<210> SEQ ID NO 17
<211> LENGTH: 17
<212> TYPE: DNA
<213> ORGANISM: Artificial Sequence
<220> FEATURE:
<223> OTHER INFORMATION: complementary probe C for hTERT

<400> SEQUENCE: 17
gccaggggat cccgcag                                                  17

<210> SEQ ID NO 18

```
<211> LENGTH: 22
<212> TYPE: DNA
<213> ORGANISM: Artificial Sequence
<220> FEATURE:
<223> OTHER INFORMATION: TaqMan probe

<400> SEQUENCE: 18
ccctgcggga tccctggca ct                                               22

<210> SEQ ID NO 19
<211> LENGTH: 36
<212> TYPE: DNA
<213> ORGANISM: Artificial Sequence
<220> FEATURE:
<223> OTHER INFORMATION: anchor probe A for human GUSB

<400> SEQUENCE: 19
cacgaccgcg gggtggttct tgtccctacg caccac                               36

<210> SEQ ID NO 20
<211> LENGTH: 83
<212> TYPE: DNA
<213> ORGANISM: Artificial Sequence
<220> FEATURE:
<223> OTHER INFORMATION: template probe B for human GUSB

<400> SEQUENCE: 20
gactgactcc tggcatcctc ggctcttggt gacagccaca gtgcggatcc ccacagggag     60
tgtcgtcgca ggtccagaga agg                                             83

<210> SEQ ID NO 21
<211> LENGTH: 18
<212> TYPE: DNA
<213> ORGANISM: Artificial Sequence
<220> FEATURE:
<223> OTHER INFORMATION: complementary probe C for human GUSB

<400> SEQUENCE: 21
tgtggggatc cgcactgt                                                   18

<210> SEQ ID NO 22
<211> LENGTH: 23
<212> TYPE: DNA
<213> ORGANISM: Artificial Sequence
<220> FEATURE:
<223> OTHER INFORMATION: TaqMan probe

<400> SEQUENCE: 22
gccacagtgc ggatccccac agg                                             23

<210> SEQ ID NO 23
<211> LENGTH: 33
<212> TYPE: DNA
<213> ORGANISM: Artificial Sequence
<220> FEATURE:
<223> OTHER INFORMATION: anchor probe A for human Bcl-2

<400> SEQUENCE: 23
gcacctctcg cccagctcc caccccacgg ccc                                   33

<210> SEQ ID NO 24
<211> LENGTH: 73
<212> TYPE: DNA
<213> ORGANISM: Artificial Sequence
<220> FEATURE:
<223> OTHER INFORMATION: template probe B for human Bcl-2
```

-continued

<400> SEQUENCE: 24
gactgactcc tggcatcctc ggggcagccg gggtctgcag cggcgaggtc cgtcgtcgca    60
ggtccagaga agg    73

<210> SEQ ID NO 25
<211> LENGTH: 16
<212> TYPE: DNA
<213> ORGANISM: Artificial Sequence
<220> FEATURE:
<223> OTHER INFORMATION: complementary probe C for human Bcl-2

<400> SEQUENCE: 25
tcgccgctgc agaccc    16

<210> SEQ ID NO 26
<211> LENGTH: 37
<212> TYPE: DNA
<213> ORGANISM: Artificial Sequence
<220> FEATURE:
<223> OTHER INFORMATION: anchor probe A for human PAR-2

<400> SEQUENCE: 26
gtgctaggat tacaggcatg aggcaccgca cccagcc    37

<210> SEQ ID NO 27
<211> LENGTH: 81
<212> TYPE: DNA
<213> ORGANISM: Artificial Sequence
<220> FEATURE:
<223> OTHER INFORMATION: template probe B for human PAR-2

<400> SEQUENCE: 27
gactgactcc tggcatcctc ggttccttgg atggtgccac tgcaggagag agaggctgcg    60
tcgtcgcagg tccagagaag g    81

<210> SEQ ID NO 28
<211> LENGTH: 19
<212> TYPE: DNA
<213> ORGANISM: Artificial Sequence
<220> FEATURE:
<223> OTHER INFORMATION: complementary probe C for human PAR-2

<400> SEQUENCE: 28
tctctcctgc agtggcacc    19

<210> SEQ ID NO 29
<211> LENGTH: 35
<212> TYPE: DNA
<213> ORGANISM: Artificial Sequence
<220> FEATURE:
<223> OTHER INFORMATION: anchor probe A for human hRPLP0

<400> SEQUENCE: 29
gcaggagcag ctgtggtggc agcagccaca ggggc    35

<210> SEQ ID NO 30
<211> LENGTH: 80
<212> TYPE: DNA
<213> ORGANISM: Artificial Sequence
<220> FEATURE:
<223> OTHER INFORMATION: template probe B for human hRPLP0

<400> SEQUENCE: 30
gactgactcc tggcatcctc gggtagccaa tctgcagaca gacactggca acattgcggt    60
cgtcgcaggt ccagagaagg                                                80

<210> SEQ ID NO 31
<211> LENGTH: 21
<212> TYPE: DNA
<213> ORGANISM: Artificial Sequence
<220> FEATURE:
<223> OTHER INFORMATION: complementary probe C for human hRPLP0

<400> SEQUENCE: 31
gtgtctgtct gcagattggc t                                              21

<210> SEQ ID NO 32
<211> LENGTH: 35
<212> TYPE: DNA
<213> ORGANISM: Artificial Sequence
<220> FEATURE:
<223> OTHER INFORMATION: template probe B for human hGAPDH

<400> SEQUENCE: 32
tgccagtgag cttcccgttc agctcaggga tgacc                               35

<210> SEQ ID NO 33
<211> LENGTH: 83
<212> TYPE: DNA
<213> ORGANISM: Artificial Sequence
<220> FEATURE:
<223> OTHER INFORMATION: template probe B for human hGAPDH

<400> SEQUENCE: 33
gactgactcc tggcatcctc ggatttccat tgatgacaag cttcccgttc tcagccttga    60
cgtcgtcgca ggtccagaga agg                                            83

<210> SEQ ID NO 34
<211> LENGTH: 19
<212> TYPE: DNA
<213> ORGANISM: Artificial Sequence
<220> FEATURE:
<223> OTHER INFORMATION: complementary probe C for human hGAPDH

<400> SEQUENCE: 34
aacgggaagc ttgtcatca                                                 19

<210> SEQ ID NO 35
<211> LENGTH: 37
<212> TYPE: DNA
<213> ORGANISM: Artificial Sequence
<220> FEATURE:
<223> OTHER INFORMATION: anchor probe A for human ZO1

<400> SEQUENCE: 35
ggctctgacc gctggtcagg agatcgtgac cggctgc                             37

<210> SEQ ID NO 36
<211> LENGTH: 92
<212> TYPE: DNA
<213> ORGANISM: Artificial Sequence
<220> FEATURE:
<223> OTHER INFORMATION: template probe B for human ZO1

<400> SEQUENCE: 36
gactgactcc tggcatcctc ggttctgcct catcatttcc tcgggatatg gatcctttct    60
atacaccttt gtcgtcgcag gtccagagaa gg                                  92

<210> SEQ ID NO 37
<211> LENGTH: 21
<212> TYPE: DNA
<213> ORGANISM: Artificial Sequence
<220> FEATURE:
<223> OTHER INFORMATION: complementary probe C for human ZO1

<400> SEQUENCE: 37
gaaaggatcc atatcccgag g                                                    21

<210> SEQ ID NO 38
<211> LENGTH: 33
<212> TYPE: DNA
<213> ORGANISM: Artificial Sequence
<220> FEATURE:
<223> OTHER INFORMATION: anchor probe A for human hTERC

<400> SEQUENCE: 38
ccgagtcctg ggtgcacgtc ccacagctca ggg                                       33

<210> SEQ ID NO 39
<211> LENGTH: 74
<212> TYPE: DNA
<213> ORGANISM: Artificial Sequence
<220> FEATURE:
<223> OTHER INFORMATION: template probe B for human hTERC

<400> SEQUENCE: 39
ccttctctgg acctgcgacg actccggaga agccccgggc cgaccgcggc ctccgaggat          60
gccaggagtc agtc                                                            74

<210> SEQ ID NO 40
<211> LENGTH: 16
<212> TYPE: DNA
<213> ORGANISM: Artificial Sequence
<220> FEATURE:
<223> OTHER INFORMATION: complementary probe C for human hTERC

<400> SEQUENCE: 40
gtcggcccgg ggcttc                                                          16

<210> SEQ ID NO 41
<211> LENGTH: 33
<212> TYPE: DNA
<213> ORGANISM: Artificial Sequence
<220> FEATURE:
<223> OTHER INFORMATION: anchor probe A for mouse beta-actin

<400> SEQUENCE: 41
ccttccccgg ggtggactca gggcatggac gcg                                       33

<210> SEQ ID NO 42
<211> LENGTH: 75
<212> TYPE: DNA
<213> ORGANISM: Artificial Sequence
<220> FEATURE:
<223> OTHER INFORMATION: template probe B for mouse beta-actin

<400> SEQUENCE: 42
gactgactcc tggcatcctc ggggaataca gcccggggag catcgtcgcc cgcgtcgtcg          60
caggtccaga gaagg                                                           75

<210> SEQ ID NO 43

```
<211> LENGTH: 18
<212> TYPE: DNA
<213> ORGANISM: Artificial Sequence
<220> FEATURE:
<223> OTHER INFORMATION: complementary probe C for mouse beta-actin

<400> SEQUENCE: 43
atgctccccg ggctgtat                                                    18

<210> SEQ ID NO 44
<211> LENGTH: 36
<212> TYPE: DNA
<213> ORGANISM: Artificial Sequence
<220> FEATURE:
<223> OTHER INFORMATION: anchor probe A for mouse Col4a1

<400> SEQUENCE: 44
ccgtacccaa gtcctgcccg tgggcacgct cgttgc                                36

<210> SEQ ID NO 45
<211> LENGTH: 79
<212> TYPE: DNA
<213> ORGANISM: Artificial Sequence
<220> FEATURE:
<223> OTHER INFORMATION: template probe B for mouse Col4a1

<400> SEQUENCE: 45
ccttctctgg acctgcgacg acctggggga cccatggatc ctggcagccc atcggggccg      60
aggatgccag gagtcagtc                                                   79

<210> SEQ ID NO 46
<211> LENGTH: 18
<212> TYPE: DNA
<213> ORGANISM: Artificial Sequence
<220> FEATURE:
<223> OTHER INFORMATION: complementary probe C for mouse Col4a1

<400> SEQUENCE: 46
tgccaggatc catgggtc                                                    18

<210> SEQ ID NO 47
<211> LENGTH: 37
<212> TYPE: DNA
<213> ORGANISM: Artificial Sequence
<220> FEATURE:
<223> OTHER INFORMATION: anchor probe A for mouse Wrn

<400> SEQUENCE: 47
tttctcctgc aggatgtcca cagcagacag tagctgg                               37

<210> SEQ ID NO 48
<211> LENGTH: 88
<212> TYPE: DNA
<213> ORGANISM: Artificial Sequence
<220> FEATURE:
<223> OTHER INFORMATION: template probe B for mouse Wrn

<400> SEQUENCE: 48
gactgactcc tggcatcctc ggaaggagca atcactagct tcataactgt aaacaatgga      60
tccagggtcg tcgcaggtcc agagaagg                                         88

<210> SEQ ID NO 49
<211> LENGTH: 21
<212> TYPE: DNA
<213> ORGANISM: Artificial Sequence
```

```
<220> FEATURE:
<223> OTHER INFORMATION: complementary probe C for mouse Wrn

<400> SEQUENCE: 49
tccctggatc cattgtttac a                                              21

<210> SEQ ID NO 50
<211> LENGTH: 33
<212> TYPE: DNA
<213> ORGANISM: Artificial Sequence
<220> FEATURE:
<223> OTHER INFORMATION: anchor probe A for ampicillin resistance gene

<400> SEQUENCE: 50
ccagccagcc ggaagggccg agcgcagaag tgg                                 33

<210> SEQ ID NO 51
<211> LENGTH: 83
<212> TYPE: DNA
<213> ORGANISM: Artificial Sequence
<220> FEATURE:
<223> OTHER INFORMATION: template probe B for ampicillin resistance gene

<400> SEQUENCE: 51
gactgactcc tggcatcctc ggggcgaaaa ctctcaagga tcttaccgct gttgagatcc    60
agtcgtcgca ggtccagaga agg                                            83

<210> SEQ ID NO 52
<211> LENGTH: 27
<212> TYPE: DNA
<213> ORGANISM: Artificial Sequence
<220> FEATURE:
<223> OTHER INFORMATION: complementary probe C for ampicillin resistance
      gene

<400> SEQUENCE: 52
ctggatctca acagcggtaa gatcctt                                        27
```

WASHING-FREE TEMPLATE-READY PCR DETECTION METHOD FOR RNA

TECHNICAL FIELD

The present application relates to a washing-free template-ready PCR process for detecting RNA.

BACKGROUND

RT-PCR (Reverse Transcription Polymerase Chain Reaction) is a method that combines Reverse Transcription (RT) with PCR (Polymerase Chain Reaction). By combining cDNA synthesis with RNA as the template, e.g. RT, with PCR amplification, RT-PCR provides a rapid and sensitive method for the analysis of gene expression. RT-PCR detection or quantitative analysis of RNA is more sensitive and much easier to operate than other RNA analysis techniques such as Northern blotting, RNase protection analysis, hybridization in situ, and S1 nuclease analysis, and it has developed into a powerful means for detecting and analyzing gene expression levels and pathogens. However, in the application of RT-PCR, we have also encountered some problems, such as: high requirement for the purity of RNA sample—it requires not only the removal of non-nucleic acid substance such as protein, but also the removal of DNA in order to avoid interference of DNA; because it involves multiple operating procedures and long period of operation, it needs special care to prevent RNA degradation in the operation; since the two enzymatic reactions (RT and PCR) have different optimal reaction conditions, it is not easy to find an optimal balance point; all these issues lead to complicated procedure, high operating requirements and render it susceptible to various inhibitory substances and the trouble of non-specific amplification and false positive result. Meanwhile, the cost of reverse transcriptase has been always high and it is difficult to lower the implementation cost of this process. To sum up, the method has troublesome to carry out and the cost is high, resulting in difficulty in its clinical popularity.

Template-Ready PCR (TRPCR) is a RNA PCR detection method recently reported by the applicant (CN102864233A). In this method, an anchored probe is used to specifically bind with the target RNA, and another template probe that binds with target RNA is adsorbed and immobilized in the reaction tube, after repeated washing steps, unbound RNA and other substances are removed and a PCR reaction system is added for PCR amplification of the template probe, and the result can reflect the situation of presence of target RNA. Compared to traditional RT-PCR method, this process does not need purification and extraction of RNA or reverse transcription reaction, on the other hand, it decreases the previously three hours of PCR pretreatment process to be 50 minutes. So it is simple, rapid and easy to operate, with good detection sensitivity and specificity for RNA, and is suitable for detecting RNA obtained from the lysate of various sources. While in practical application, the inventor has found that multiple washing steps of TRPCR are still complicated, and there is high requirement for temperature control of binding between template probe and target RNA and the procedure is easily influenced by the environmental temperature; if the room temperature is too low, then non-specific binding occurs, resulting in false positive result and bringing unstable and inconsistent factor to the result. Therefore the inventor has redesigned the TRPCR process and made major innovative improvement thereto by introducing a double-stranded DNA-specific digestion reaction.

SUMMARY

A washing-free template-ready PCR process for detecting RNA is provided, which is easy and quick to operate and has good specificity.

The technical solution of the present application is carried out as follows:

a washing-free template-ready PCR process for detecting RNA comprising:

(1) Design and synthesis of a single-stranded oligonucleotide DNA with a length of 25-50 mer complementary to any section of a target RNA sequence, marked as probe A; wherein the probe A has a GC content of 40% to 60%, and a melting temperature (Tm value) of 75 to 85° C.; the probe A being anchored into a PCR tube to give an anchored PCR tube; wherein the probe A can be immobilized with a conventional method in the art, and the solid medium used to bind to the anchored probe A can be a plastic centrifuge tube, or a magnetic bead, a gel particle or any other solid medium that can be connected to a nucleic acid by absorption; the probe A is preferably a biotinylated probe A, i.e. a biotin is added directly onto the 5' end by modification in the synthesis process; in particular, the preparation method of the anchored PCR tube can be carried out as follows: 20 ul of TBST buffer containing 5 pmol of biotinylated anchor probe A is added into a 0.2 ml thin-walled PCR tube coated with streptavidin, and incubated at room temperature for 1 hr, the liquid in the tube is removed out, and 100 μl of TBST buffer is added, mixed well, the liquid is removed out, this step is repeated for another two times, then the liquid is removed out; 100 μl of TE buffer is added, then the inner liquid is removed out, stocked at −20° C. before sealing.

(2) Design and synthesis of another single-stranded oligonucleotide DNA with a length of 70 to 100 mer partially complementary to another section of a target RNA sequence containing a restriction endonuclease recognition site, which has the following construction: in the middle is a sequence of 25 to 50 mer completely complementary to a region containing the restriction endonuclease recognition site (Region 2) of the target RNA, at both ends are PCR primer sequences with a length of 20 to 30 mer respectively, this single-stranded oligonucleotide DNA is marked as probe B; wherein the probe B has a GC content of 40% to 60%, a melting temperature of from 75 to 85° C., and it has no overlap with the region of probe A binding to target RNA; the restriction endonuclease has the following characteristics: it does not cut RNA/DNA hybrid duplex (double strand), it remains specific double-stranded DNA cleavage activity at 37° C. in a PCR system, while losses activity at a temperature ≥55° C., it can be, for example, PstI, BamHI, EcoRI, HindIII, AvaI, MboI or the like.

(3) Design and synthesis of a single-stranded oligonucleotide DNA of 15 to 30 mer, marked as complementary probe C; wherein this probe is completely complementary to a part (Region 3) of the sequence (Region 2) containing the restriction endonuclease recognition site of the above said probe B; its melting temperature is 50 to 60° C.; the double-stranded DNA fragment formed with this probe binding to the template probe B can be cleaved by the above restriction endonuclease; Region 3 has a length smaller than that of Region 2, and it is totally included into Region 2, so that the binging temperature of the complementary probe C to the template probe B is 20° C. to 25° C. lower than that of the template probe B to the target RNA.

(4) Taking the sample to be tested, the template probe B, complementary probe C and lysis buffer are added, mixed by repeated pipetting, the obtained mixture is transferred to a centrifuge tube, shaken at room temperature for 10 min, centrifuged at 4° C., the supernatant is taken to give a lysate supernatant; wherein the lysis buffer is a conventional buffer in the art which contains a surfactant (e.g. Tween 20, Triton X-100, NP-40, and the like) for lysing cell or tissue.

The sample to be tested can be obtained from tissues or cells, or clinical samples such as luggies (sputum), blood and the like.

When the sample to be tested is obtained from luggies (sputum), the preparation method of lysate supernatant is carried out as follows: prepare 1 to 5 ml sputum+5 to 10 ml sputum lysis buffer, the obtained mixture is vibrated at 37° C. for 10 min, then centrifuged at 4° C., 5000 rpm for 10 min, the supernatant is discarded, 200 ul of lysis buffer (wherein the concentrations of the template probe B and complementary probe C are both 0.1 nmol/L) is added to the precipitate, treated by repeated pipetting and transferred to a 1.5 ml centrifuge tube, it is shaken at room temperature for 10 min, then centrifuged at 4° C., 15000 rpm for 20 min, supernatant is taken to give supernatant of lysate; the composition of the sputum lysis buffer is: PBS+0.1% (w/vol) DTT.

When the sample to be tested is obtained from cells, the method for obtaining lysate supernatant is carried out as follows: 24-well plate is employed for cell culture, the culture medium is taken out, 200 ul of lysis buffer (where the concentrations of the probe B and the complementary probe C are both 0.1 nmol/L) is added, the obtained mixture is treated by repeated pipetting and transferred to a 1.5 ml centrifuge tube, shaken at room temperature for 10 min, centrifuged at 4° C., 15000 rpm for 20 min, the supernatant is taken to give supernatant of lysate.

When the sample to be tested is obtained from a tissue, the method for obtaining lysate supernatant is as follows: a tissue of 0.1 cm$^3$ in size is put into 1.5 ml centrifuge tube, 200 ul of lysis buffer (wherein the concentrations of template probe B and the complementary probe C are both 0.1 nmol/L) is added, the tissue is broken with a tip, then the obtained mixture is shaken at room temperature for 10 min, centrifuged at 4° C., 15000 rpm for 20 min, the supernatant is taken as lysate supernatant.

(5) 20 uL of the obtained lysate supernatant is added into the anchor PCR tube, incubated at 55 to 65° C. for 10 to 30 min, the liquid in the tube is removed out, 20 uL of RE/PCR reaction solution consisting of PCR buffer, dNTP, Taq enzyme, PCR primers (which are a pair of primers identical to both ends of the probe B, respectively, the solution thereof is 0.2 umol/L), SYBR green I, or TaqMan fluorescent probe, and the above said restriction endonuclease is added to perform PCR amplification, the amplified product is subjected to fluorescent quantitative analysis; the PCR reaction condition is as follows: 37° C. for 5 to 20 min, 92 to 95° C. for 2 to 5 min, then 35 to 40 cycles of 92 to 95° C. for 3 to 30 sec, and 55 to 66° C. for 20 to 60 sec; the buffer is a conventional PCR reaction buffer; the step of taking out (sucking out) liquid can remove such substances that may interfere with the PCR reaction, the integrated cleavage reaction can prevent not only the interference of the template probe B not hybridized to target RNA to the PCR reaction, but also the cross-contamination caused by aerosol diffusion of trace PCR product, so as to ensure the specificity and the success rate of the PCR reaction.

(6) Taking (blank) lysate as a negative control, it is subjected the treatment and analysis of the above steps (4) and (5), the sample with sample Ct value being smaller than the Ct value of (blank) lysate and the absolute value of the difference between them being equal to or greater than 1 is determined as positive.

According to the present invention, an anchor probe A is employed to bind to and immobilize the target RNA, another template probe B is used to bind to the target RNA, meanwhile an auxiliary complementary probe C is used to complementarily bind to the remaining template probe B that is not bound to the target RNA, wherein the double-stranded DNA structure formed by the template probe B binding the complementary probe C contains a restriction endonuclease cleavage site, as the restriction endonuclease has a good activity in the PCR system, it does not cleave RNA/DNA hybrid duplexes, after the hybridization reaction is finished and the hybridization reaction solution is removed out, a PCR system containing the restriction endonuclease is added, and incorporate a step of keeping temperature to maintain enzyme cleavage into this process prior to the PCR reaction procedure, in this process the double stranded DNA formed by the remaining template probe B binding to a complementary probe C rather than a target RNA is cleaved by the enzyme, and only the template probe B bound to a target RNA remains intact, and amplified in the subsequent PCR reaction. The fluorescent dye SYBR green I, or TaqMan Fluorescent probe contained in this system can be used for performing the real-time quantitative PCR reaction, the said enzyme cleavage reaction and the PCR reaction are carrier out continuously in a whole system, which does not require additional operation such as changing fluid.

Preferably, the lysis buffer in step (4) has the following composition: 4.0 mol/L of guanidine isothiocyanate, 350 mmol/L of NaCl, 1% (v/v) of Triton X-100, 10 mmol/L of 2-mercaptoethanol, 0.1 mg/ml of salmon sperm DNA (commercially available), the solvent is 10 mmol/L of Tris-HCl with pH of 7.5.

Preferably, the RE/PCR reaction solution of the step (5) has the following composition: 50 mmol/L of KCl, 1.5 mmol/L of MgCl$_2$, 0.2 mmol/L of dNTP, 0.05% (v/v) of Tween20, 0.4×SYBR Green I (the meaning of "0.4×" concentration is: the final concentration of each component in the reaction mixture is 0.4 times of the final concentration of that in 1×SYBR Green I solution, while the stock solution of SYBR Green I purchased from Microprobe is 10000×, so the final solution thereof is diluted by volume to be 0.4× when used for PCR process), 0.5 U/20 uL of Taq enzyme, 4 U/20 uL of restriction endonuclease, 0.2 umol/L of PCR universal primer, the solvent is 10 mmol/L of Tris-HCl with pH of 9.0.

The following is specific description of a target gene, restriction endonuclease for primer and probe sequences in specific detection process:

The general PCR primer sequences are optimized general sequences as follows: 5'-GACTGACTCCTGGCATC-CTCGG-3' (SEQ ID NO: 1) and 5'-CCTTCTCTGGACCT-GCGACGAC-3' (SEQ ID NO: 2);

When the inventive process is used for detecting human DKK1 gene, the anchor probe A has the following sequence: 5'-CCGTTCTTGTAGAACACACACATACGTACACA-CACACAAACCTC-3' (SEQ ID NO: 3), the template probe B has the following sequence: 5'-GACTGACTCCTG-GCATCCTCGGCGCTTCCTGCAGGCGAGACAGATTT-GCACG CCTGCGTCGTCGCAGGTCCAGAGAAGG-3' (SEQ ID NO: 4), and the complementary probe C has the following sequence: 5'-TCGCCTGCAGGAAGCG-3' (SEQ ID NO: 5), wherein the highlighted italicized sequence is the recognition site of PstI, and the restriction endonuclease is PstI.

When the said process is used for detecting human TLR2 gene, the anchor probe A has the following sequence: 5'-GTTGGCCCTCTATATCCATGGGTTCTGCATCCAT-GAAGTC-3' (SEQ ID NO: 6), the template probe B has the following sequence: 5'-CCTTCTCTGGACCTGCGAC-GACTATGAATTTTGATATCCACGAGGATCCTGCA ACCAATTCCCGAGGATGCCAGGAGTCAGTC-3' (SEQ ID NO: 7), and the complementary probe C has the following sequence: 5'-GTTGCAGGATCCTCGTGGA-3' (SEQ ID NO: 8), wherein the highlighted italicized sequence is the recognition site of BamHI, and the restriction endonuclease is BamHI.

When the said process is used for detecting human TLR7 gene, the anchor probe A has the following sequence: 5'-CCATCTTGGGGGCACATGCTGAAGAGAGTTA CTGTG-3' (SEQ ID NO. 9), the template probe B has the following sequence: 5'-GACTGACTCCTGGCATCCTCG-GTGATTTCCTCTGAATTCCAGAGTTCTA AGAGACT-CACTCTCCATGGTCGTCGCAGGTCCAGAGAAGG-3' (SEQ ID NO: 10), and the complementary probe C has the following sequence: 5'-AACTCTGGAATTCAGAG-GAAAT-3' (SEQ ID NO: 11), wherein the highlighted italicized sequence is the recognition site of EcoRI, and the restriction endonuclease is EcoRI.

When the said process is used for detecting human XRCC6, the anchor probe A has the following sequence: 5'-CCAGCGACTCCTCTGGGTACACGAACAGGGAG GGCC-3' (SEQ ID NO: 12), the template probe B has the following sequence: 5'-CCTTCTCTGGACCTGCGAC-GACTGGTCAAGCTCTAGAATTCGTTTTGCACCTG GATTATCCGAGGATGCCAGGAGTCAGTC-3' (SEQ ID NO: 13), and the complementary probe C has the following sequence: 5'-GCAAAACGAATTCTAGAGCTT-3' (SEQ ID NO: 14), wherein the highlighted italicized sequence is the recognition site of EcoRI, and the restriction endonuclease is EcoRI.

When the said process is used for detecting human telomerase reverse transcriptase (hTERT), the anchor probe A has the following sequence: 5'-GGTGCGGGCCTGGGT-GTGGGCCGCCCCTCC-3' (SEQ ID NO: 15), the template probe B has the following sequence: 5'-GACTGACTCCTG-GCATCCTCGGATGGAGCCCTGCGGGATCCCCTG-GCACTGG ACGTCGTCGCAGGTCCAGAGAAGG-3' (SEQ ID NO: 16), and the complementary probe C has the following sequence: 5'-GCCAGGGGATCCCGCAG-3' (SEQ ID NO: 17), wherein the highlighted italicized sequence is recognition site of BamHI, and the restriction endonuclease is BamHI. The sequence of TaqMan probe is as follows: 5'-FAM-CCCTGCGGGATCCCCTGGCACT-BHQ1-3' (SEQ ID NO: 18).

When the said process is used for detecting human GUSB gene, the anchor probe A has the following sequence: 5'-CACGACCGCGGGGTGGTTCTTGTCCCTAC GCAC-CAC-3' (SEQ ID NO: 19), the template probe B has the following sequence: 5'-GACTGACTCCTGGCATCCTCG-GCTCTTGGTGACAGCCACAGTGCGGATCCCCA CAGGGAGTGTCGTCGCAGGTCCAGAGAAGG-3' (SEQ ID NO: 20), and the complementary probe C has the following sequence: 5'-TGTGGGGATCCGCACTGT-3' (SEQ ID NO 21), wherein the highlighted italicized sequence is the recognition site of BamHI, and the, and the restriction endonuclease is BamHI. The sequence of the TaqMan probe is SEQ ID NO: 22 (5'-FAM-GCCACAGT-GCGGATCCCCACAGG-BHQ1-3' (FAM is the fluorophore, and BHQ1 is the quencher)).

When the said process is used for detecting human Bcl-2 gene, the anchor probe A has the following sequence: 5'-GCACCTCTCGCCCCAGCTCCCACCCCACGGCCC-3' (SEQ ID NO: 23), the template probe B has the following sequence: 5'-GACTGACTCCTGGCATCCTCGGGGCA-GCCGGGGTCTGCAGCGGCGAGGTCCG TCGTCGCA-GGTCCAGAGAAGG-3' (SEQ ID NO 24), and the complementary probe C has the following sequence: 5'-TCGCCGCTGCAGACCC-3' (SEQ ID NO 25), wherein the highlighted italicized sequence is the recognition site of PstI, and the restriction endonuclease is PstI.

When the said process is used for detecting human PAR-2gene, the anchor probe A has the following sequence: 5'-GTGCTAGGATTACAGGCATGAGGCACCGCAC-CCAGCC-3' (SEQ ID NO: 26), the template probe B has the following sequence: 5'-GACTGACTCCTGGCATCCTCG-GTTCCTTGGATGGTGCCACTGCAGGAGAGAG AGGCTGCGTCGTCGCAGGTCCAGAGAAGG-3' (SEQ ID NO: 27), and the complementary probe C has the following sequence: 5'-TCTCTCCTGCAGTGGCACC-3' (SEQ ID NO: 28), wherein the highlighted italicized sequence is the recognition site of PstI, and the restriction endonuclease is PstI.

When the said process is used for detecting human hRPLPO gene, the anchor probe A has the following sequence: 5'-GCAGGAGCAGCTGTGGTGGCAGCAGC-CACAGGGGC-3' (SEQ ID NO: 29), the template probe B has the following sequence: 5'-GACTGACTCCTGGCATC-CTCGGGTAGCCAATCTGCAGACAGACACTGGCAAC ATTGCGGTCGTCGCAGGTCCAGAGAAGG-3' (SEQ ID NO: 30), and the complementary probe C has the following sequence: 5'-GTGTCTGTCTGCAGATTGGCT-3' (SEQ ID NO: 31), wherein the highlighted italicized sequence is the recognition site of PstI, and the restriction endonuclease is PstI.

When the said process is used for detecting human hGAPDH gene, the anchor probe A has the following sequence: 5'-TGCCAGTGAGCTTCCCGTTCAGCTCA-GGGATGACC-3' (SEQ ID NO: 32), the template probe B has the following sequence: 5'-GACTGACTCCTGGCATC-CTCGGATTTCCATTGATGACAAGCTTCCCGTTCTCA GCCTTGACGTCGTCGCAGGTCCAGAGAAGG-3 (SEQ ID NO: 33), and the complementary probe C has the following sequence: 5'-AACGGGAAGCTTGTCATCA-3' (SEQ ID NO 34), wherein the highlighted italicized sequence is the recognition site of HindIII, and-the restriction endonuclease is HindIII.

When the said process is used for detecting human ZO1 gene, the anchor probe A has the following sequence: 5'-GGCTCTGACCGCTGG TCA GGAGATCGTGACCG-GCTGC-3' (SEQ ID NO: 35), the template probe B has the following sequence: 5'-GACTGACTCCTGGCATCCTCG-GTTCTGCCTCATCATTTCCTCGGGATATGGAT CCTTTCTATACACCTTTGTCGTCGCAGGTCCAGA-GAAGG-3' (SEQ ID NO: 36), and the complementary probe C has the following sequence: 5'-GAAAGGATCCATATC-CCGAGG-3' (SEQ ID NO 37), wherein the highlighted italicized sequence is the recognition site of BamHI, and the restriction endonuclease is BamHI.

When the said process is used for detecting human hTERC gene, the anchor probe A has the following sequence: 5'-CCGAGTCCTGGGT G C A CGTCCCACA-GCTCAGGG-3' (SEQ ID NO: 38), the template probe B has the following sequence: 5'-CCTTCTCTGGACCTGCGAC-GACTCCGGAGAAGCCCCGGGCCGACCGCGGCCT CCGAGGATGCCAGGAGTCAGTC-3' (SEQ ID NO: 39), and the complementary probe C has the following sequence: 5'-GTCGGCCCGGGGCTTC-3' (SEQ ID NO: 40), wherein the highlighted italicized sequence is the recognition site of AvaI, and the restriction endonuclease is AvaI.

When the said process is used for detecting mouse beta-actin gene, the anchor probe A has the following sequence: 5'-CCTTCCCCGGGGTGGACTCAGGGCATGGACGCG-3' (SEQ ID NO: 41), the template probe B has the following sequence: 5'-GACTGACTCCTGGCATCCTCGGGGAATACAGCCCGGGGAGCATCGTCGCCCGCGTCGTCGCAGGTCCAGAGAAGG-3' (SEQ ID NO: 42), and the complementary probe C has the following sequence: 5'-ATGCTCCCCGGGCTGTAT-3' (SEQ ID NO: 43), the highlighted italicized sequence is the recognition site of AvaI, and the restriction endonuclease is AvaI.

When the said process is used for detecting mouse Col4a1 gene, the anchor probe A has the following sequence: 5'-CCGTACCCAAGTCCTGCCCGTGGGCACGCTCGT-TGC-3' (SEQ ID NO: 44), the template probe B has the following sequence: 5'-CCTTCTCTGGACCTGCGAC-GACCTGGGGGACCCATGGATCCTGGCAGCCCAT CGGGGCCGAGGATGCCAGGAGTCAGTC-3' (SEQ ID NO: 45), and the complementary probe C has the following sequence: 5'-TGCCAGGATCCATGGGTC-3' (SEQ ID NO: 46), wherein the highlighted italicized sequence is the recognition site of BamHI, and the restriction endonuclease is BamHI.

When the said process is used for detecting mouse Wrn gene, the anchor probe A has the following sequence: 5'-TTTCTCCTGCAGGATGTCCACAGCAGACAG-TAGCTGG-3' (SEQ ID NO: 47), the template probe B has the following sequence: 5'-GACTGACTCCTGGCATC-CTCGGAAGGAGCAATCACTAGCTTCATAACTGTAA ACAATGGATCCAGGGTCGTCGCAGGTCCAGA-GAAGG-3' (SEQ ID NO: 48), and the complementary probe C has the following sequence: 5'-TCCCTGGATCCATT-GTTTACA-3' (SEQ ID NO: 49), wherein the highlighted italicized sequence is the recognition site of BamHI, and the restriction endonuclease is BamHI.

When the said process is used for detecting the ampicillin resistance gene expressed by *E. coli*, the anchor probe A has the following sequence: 5'-CCAGCCAGCCGGAAGGGC-CGAGCGCAGAAGTGG-3' (SEQ ID NO: 50), the template probe B has the following sequence: 5'-GACT-GACTCCTGGCATCCTCGGGGCGAAAACTCTCAA-GGATCTTACCGCTGTT GAGATCCAGTCGTCGCAG-GTCCAGAGAAGG-3' (SEQ ID NO: 51), and the complementary probe C has the following sequence: 5'-CTG-GATCTCAACAGCGGTAAGATCCTT-3' (SEQ ID NO: 52), wherein the highlighted italicized sequence is the recognition site of MboI, and the restriction endonuclease is MboI.

TABLE 1

Comparison of four RNA detection methods

|  | WFTR-PCR | TRPCR | SORT-PCR | RT-PCR |
|---|---|---|---|---|
| Anchor probe/primer | + | + | + | − |
| template probe | + | + | − | − |
| complementary probe | + | − | − | − |
| Cell lysis | + | + | + | + |
| RNA Extraction | − | − | − | + |
| Use of phenol chloroform or affinity column | − | − | − | + |

TABLE 1-continued

Comparison of four RNA detection methods

|  | WFTR-PCR | TRPCR | SORT-PCR | RT-PCR |
|---|---|---|---|---|
| DNase treatment and re-extraction | − | − | − | + |
| Reverse Transcriptase enzyme and RT reaction | − | − | + | + |
| Integration of dsDNA specific enzyme digestion | + | − | + | − |
| PCR universal primer | + | + | − | − |
| PCR optimization | + | + | + | − |
| Application of cDNA clone | − | − | + | + |
| Difficulty of Operation | Simple | Simple | Simple | Complex |
| Steps from cell lysis to the result | 6 | 12 | 8 | 15 |
| Total Time (hr) | ~2 | ~2.5 | ~2.5 | ~5 |
| Comparison of costs | 0.5X | 0.4X | 0.8X | 1X |

Summary: The present invention is developed based on the inventor's two other inventions, i.e. TRPCR (Template-Ready PCR) and RDIRD (Removal of DNA contamination by Incorporated Restriction Digestion). The present invention integrates TRPCR anchor probe, template probe, and RT-free system, and creatively introduce RE/PCR system similar to the restriction endonuclease of RDIRD by using complementary probe, so as to remove the template probe that is not bound to target RNA with the enzyme digestion, avoiding the 6 steps of repeated washing in the former TR-PCR. This process preserves the advantageous effects of RNA purification free, RT free, high efficient amplification, and it is more convenient, more fast and stable to operate. Compared with the conventional RT-PCR process, it has fewer steps, less time consuming, and greatly reduces the difficulty and it has lower cost. Due to its advantage of simple operation and low cost, it is also a simple PCR process for detecting RNA compared to the inventors' another invention SORT-PCR (one-Step-lysis and One-tube RT-PCR), however, the limitation of this process is that it cannot apply for cDNA clone.

The method of the present invention does not need any washing step, therefore the operation is more convenient and fast, it has good sensitivity and specificity for RNA detection, and it is suitable for detecting the samples of various sources.

BRIEF DESCRIPTION OF THE DRAWINGS

FIG. 1 is a flowchart of the inventive process;

EXPLANATION TO THE MAIN STEPS

S0: The immobilization of the anchor probe A;
S1: Lysing cells to release RNA, wherein the lysate contains the template probe B and complementary probe C, and the probe binding region contains a restriction site (RS);
S2: The anchor probe A binds a target RNA, meanwhile the template probe B bound to the target RNA is also adsorbed; other substances are removed out, and the excess template probe B and complementary probe C bind with each other to form dsDNA;
S3: Digestion reaction, trace amount of dsDNA formed by template probe B/complementary C is cleaved, while the template probe B bound to the target RNA remains intact;
S4: PCR is carried out, wherein the template probe B is amplified.

DETAILED DESCRIPTION OF THE INVENTION

The present application will be described with following specific example, however, the protection scope of the present application is not intending to be limited thereby.

Example 1: Detection of the Expression of Human DKK1 Gene by WFTR-PCR

For probe and primer sequences, please see the section of Summary.

Preparation of anchor PCR tube: 50 ul of TBST buffer, anchor probe A containing 5 pmol of biotinylation (directly modified at the 5'end in the synthesis procedure, commercially available) were placed in 0.2 ml thin walled PCR tube coated with streptavidin (PCR tube coated with streptavidin was purchased from Roche), kept at room temperature for 1 hr, the liquid inside the tube was removed out, 100 ul of TBST buffer was added, evenly mixed, dried and washed, this step was performed for three times, and was dried at last; then 100 ul of TE buffer was added, the liquid inside the tube was removed and the tube was sealed and stocked at −20'C for future use.

RE/PCR reaction solution composition: 50 mmol/L of KCl, 1.5 mmol/L of $MgCl_2$, 0.2 mmol/L of dNTP, 0.05% (v/v) of Tween20, 0.4×SYBR Green I, 0.5 U/20 uL of Taq enzyme, 4 U/20 uL of restriction endonuclease, 0.2 umol/L of PCR universal primer, the solvent was 10 mmol/L of Tris-HCl with pH of 9.0.

Human skin cancer cell strain A431 cells were cultured in a 24-well plate, the density was 1000 cells/well. After incubation overnight, the culture medium was removed, and 200 ul of lysis buffer was added (concentrations of template probe B and complementary probe C added in the lysis buffer were 0.1 nmol/L), pipetted repeatedly and transferred to a 1.5 ml centrifuge tube, shaken at room temperature for 10 min, centrifuged at 4° C. and 15000 rpm for 20 min, supernatant was taken to obtain the cell lysate supernatant.

The lysis buffer had the following composition: 4.0 mol/L of guanidine isothiocyanate, 350 mmol/L of NaCl, 1% Triton X-100, 10 mmol/L of 2-mercaptoethanol, 0.1 mg/ml of salmon sperm DNA (Sigma), the solvent was 10 mmol/L of Tris-HCl of pH 7.5.

20 ul of above said cell lysate supernatant was taken and added into an anchored PCR tube, insulated at 60° C. for 30 min, the liquid in the tube was removed out, 20 ul of RE/PCR reaction solution (20 ul of PCR buffer +0.4×SYBR green I, 0.2 umol/L of primer pair+0.2 mmol/L of dNTP+0.5 U of Taq enzyme+4 U of PstI) was added, and the following procedure was carried out in the PCR amplifier (37'C for 10 min, initial denaturation at 95° C. for 3 min, then 40 cycles of: 95° C. for 5 s, 63° C. for 30 s, two-step method), and SYBR green I fluorescence was used for quantitative analysis. Negative control 1 was the lysate containing 0.1 nmol/L of template probe B and 0.1 nmol/L of complementary probe C, and negative control 2 was the lysate supernatant of *E. coli* DH5a (1 ml of culture medium with OD600=1.0, after centrifugation the lysate containing 0.1 nmol/L of template probe B and 0.1 nmol/L of complementary probe C was added, and supernatant was taken after lysis and centrifugation), and the result was as follows:

| Sample Group | Ct-cell | Ct- control 1 | Ct-control 2 |
| --- | --- | --- | --- |
| 1 | 27.32 | 31.36 | 31.26 |
| 2 | 27.45 | 31.20 | 30.89 |
| 3 | 27.50 | 31.42 | 30.93 |
| 4 | 27.67 | 31.55 | 31.21 |
| 5 | 27.55 | 31.39 | 30.91 |
| 6 | 27.12 | 31.68 | 30.89 |

Ct value of the cell sample was in the range of from 27.67 to 27.12, namely 27.44+/−0.23; Ct value of negative control 1, i.e. lysate, was in the range of from 31.68 to 31.20, namely 31.43+/−0.25; Ct value of negative control 2, i.e. *E. coli* lysate supernatant, was in the range of from 31.26 to 30.89, namely 31.02+/−0.17. Ct of the cell sample was significantly smaller than that of negative control 1 or negative control 2 (significantly was defined as the absolute value of difference was ≥1), indicating that WFTR-PCR can detect DKK1 mRNA of cell sample; Ct value of negative control 2 was slightly smaller than that of negative control 1, but the absolute value of difference was smaller than 1, which was within the negative fluctuation range.

Example 2: Detection of the Expression of Human TLR2 Gene by WFTR-PCR

For probe and primer sequences, please see the section of Summary, and the preparation of anchor PCR tube, the composition of RE/PCR reaction solution were the same as Example 1.

The preparation of the cell lysate supernatant of the cell samples, negative control 1 and negative control 2 were the same as Example 1, and the PstI in RE/PCR reaction solution of Example 1 was replaced with BamHI. The result was as follows:

| Sample Group | Ct-cell | Ct-control 1 | Ct-control 2 |
| --- | --- | --- | --- |
| 1 | 26.53 | 31.29 | 31.32 |
| 2 | 26.37 | 31.58 | 31.21 |
| 3 | 26.46 | 31.22 | 30.88 |
| 4 | 26.42 | 31.49 | 30.99 |
| 5 | 26.59 | 31.63 | 30.92 |
| 6 | 26.64 | 31.71 | 31.39 |

Ct value of the cell sample was 26.50+/−0.10; Ct value of negative control 1, i.e. lysate, was 31.49+/−0.19; Ct value of negative control 2, i.e. *E. coli* lysate supernatant, was 31.12+/−0.22. Ct of the cell sample was significantly smaller than that of negative control 1 or negative control 2 (significantly was defined as the absolute value of difference was ≥1), indicating that WFTR-PCR can detect TLR2 mRNA of cell sample; Ct value of negative control 2 was slightly smaller than that of negative control 1, but the absolute value of difference was smaller than 1, which was within the negative fluctuation range.

Example 3: Detection of the Expression of Human TLR7 Gene by WFTR-PCR

For probe and primer sequences, please see the section of Summary, and the preparation of anchor PCR tube, the composition of RE/PCR reaction solution were the same as Example 1.

The preparation of the cell lysate supernatant of the cell samples, negative control 1 and negative control 2 were the same as Example 1, and the PstI in RE/PCR reaction solution of Example 1 was replaced with EcoRI. The result was as follows:

| Sample Group | Ct-cell | Ct-control 1 | Ct-control 2 |
|---|---|---|---|
| 1 | 28.33 | 31.44 | 31.22 |
| 2 | 28.41 | 31.31 | 31.47 |
| 3 | 28.56 | 31.67 | 31.15 |
| 4 | 28.22 | 31.58 | 31.09 |
| 5 | 28.49 | 31.62 | 30.97 |
| 6 | 28.71 | 31.52 | 31.11 |

Ct value of the cell sample was 28.45+/−0.17; Ct value of negative control 1, i.e. lysate, was 31.52+/−0.13; Ct value of negative control 2, i.e. *E. coli* lysate supernatant, was 31.17+/−0.17. Ct of the cell sample was significantly smaller than that of negative control 1 or negative control 2 (significantly was defined as the absolute value of difference was ≥1), indicating that WFTR-PCR can detect TLR7 mRNA of cell sample; Ct value of negative control 2 was slightly smaller than that of negative control 1, but the absolute value of difference was smaller than 1, which was within the negative fluctuation range.

Example 4: Detection of the Expression of hTERT mRNA in Human Lung Cancer Cell Strain A549 by WFTR-PCR For probe and primer sequences, please see the section of Summary, and the preparation of anchor PCR tube, the composition of RE/PCR reaction solution were the same as Example 1.

BamHI was used in RE. Human lung cancer cell strain A549 was incubated in a 24-well plate, the number was from 1 to $10^6$ cells/well. After incubation overnight, the culture medium was removed, and 200 ul of lysis buffer was added (concentrations of template probe B and complementary probe C contained in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, and the PstI in RE/PCR reaction solution of Example 1 was replaced with BamHI. The result was as follows:

| Sample Group | Ct-1 | Ct-2 | Ct-Average | Determination of the result |
|---|---|---|---|---|
| 1 cell | 31.28 | 30.76 | 31.02 | negative |
| 10 cells | 28.71 | 28.53 | 28.62 | positive |
| 100 cells | 24.53 | 24.67 | 24.60 | positive |
| 1000 cells | 21.22 | 21.58 | 21.40 | positive |
| $10^5$ cells | 17.48 | 17.62 | 17.55 | positive |
| $10^6$ cells | 13.51 | 13.33 | 13.42 | positive |
| Negative control 1 | 31.63 | 31.33 | 31.48 | negative |
| Negative control 2 | 31.15 | 31.27 | 31.21 | negative |

It can be seen that using the WFTR-PCR process of the present Example, the expression of hTERT in the 10 to 106 lung cancer A549 cells can be detected, and the detection result is related with the number of cells, wherein the more the cells are, the smaller the Ct value is.

Example 5: WFTR-PCR being Used for Detecting hTERT mRNA in Sputum Specimen of Lung Cancer Patient and of Normal Person as Control With respect to probe and primer sequences, please refer to the section of Summary. The preparation of anchor PCR tube, and RE/PCR reaction solution were the same as Example 1. BamHI was used for RE.

There were 20 pathologically determined lung cancer patients and 15 normal volunteers as control, wherein the normal volunteers had sputum when smoking, had no symptom and their chest X-ray showed negative. The volume of sputum was 1 to 5 ml per person. 10 ml of sputum solution (PBS+0.1% DTT) was added, and vibrated for 10 minutes at the temperature of 37° C., then centrifuged at the speed of 5000 rpm at 4° C. for 10 minutes, the supernatant was removed, 200 ul of lysate was added to the precipitate (the same as Example 1) and pipetted repeatedly, the mixture was transferred into a 1.5 ml centrifugal tube, vibrated for 10 minutes at room temperature, and then it was centrifuged at the speed of 15000 rpm at the temperature of 4° C. for 20 minutes, the supernatant was taken to give lysate supernatant was obtained. The following operation and procedure were the same as Example 1. The lysate supernatant of 1000 A549 cells was used as positive control, and a blank lysate containing template probe B and complementary probe C was used as negative control. The determination standard of negative result was: Ct value of the sample was significantly smaller than that of lysate of negative control (significantly was defined as the absolute value of difference was ≥1), and the other results were all determined to be negative. The result showed that among the 20 lung cancer patients, 17 patients were determined to be positive and 3 patients were determined to be negative, the detection rate was 85%. The test result of 15 normal persons as control were all negative.

| No. | Age | Gender | Pathological Diagnosis | Ct value | WFTR result determination |
|---|---|---|---|---|---|
| LC001 | 60 | M | lung cancer | 30.83 | negative |
| LC002 | 59 | M | lung cancer | 23.72 | positive |
| LC003 | 61 | F | lung cancer | 24.78 | positive |
| LC004 | 60 | M | lung cancer | 23.89 | positive |
| LC005 | 76 | M | lung cancer | 26.54 | positive |
| LC006 | 59 | M | lung cancer | 25.59 | positive |
| LC007 | 60 | M | lung cancer | 31.42 | negative |
| LC008 | 58 | F | lung cancer | 26.10 | positive |
| LC009 | 67 | M | lung cancer | 32.02 | negative |
| LC010 | 57 | M | lung cancer | 25.55 | positive |
| LC011 | 74 | M | lung cancer | 27.64 | positive |
| LC012 | 47 | F | lung cancer | 31.16 | negative |
| LC013 | 60 | F | lung cancer | 26.00 | positive |
| LC016 | 49 | M | lung cancer | 22.72 | positive |
| LC017 | 65 | M | lung cancer | 19.18 | positive |
| LC018 | 53 | M | lung cancer | 15.41 | positive |
| LC019 | 64 | F | lung cancer | 27.36 | positive |
| LC020 | 60 | F | lung cancer | 21.21 | positive |
| NC001 | 55 | M | normal | 31.83 | negative |
| NC002 | 30 | M | normal | 30.72 | negative |
| NC003 | 38 | F | normal | 31.78 | negative |
| NC004 | 42 | M | normal | 30.89 | negative |
| NC005 | 46 | F | normal | 31.54 | negative |
| NC006 | 69 | M | normal | 31.59 | negative |
| NC007 | 66 | M | normal | 30.98 | negative |
| NC008 | 61 | M | normal | 31.10 | negative |
| NC009 | 72 | M | normal | 32.07 | negative |
| NC010 | 33 | F | normal | 31.55 | negative |
| NC011 | 41 | F | normal | 30.64 | negative |
| NC012 | 29 | M | normal | 32.16 | negative |
| NC013 | 35 | M | normal | 32.00 | negative |
| NC014 | 36 | M | normal | 31.49 | negative |
| NC015 | 39 | M | normal | 31.67 | negative |

-continued

| No. | Age | Gender | Pathological Diagnosis | Ct value | WFTR result determination |
|---|---|---|---|---|---|
| − | | | Negative control | 31.54 | negative |
| + | | | Positive control | 26.67 | positive |

Example 6: Detection of hTERT mRNA in Human Lung Cancer Tissue

For the sequences of probe and primer, please refer to the section of Summary, and the preparation of anchor PCR tube, RE/PCR reaction solution were the same as Example 1. BamHI was used for RE. For the above 20 lung cancer patients with confirmed diagnosis, after being cut down in a surgery, the lung cancer tissues were immediately stored in liquid nitrogen. The cancer tissue was subjected to pathological determination. A tissue of about 0.1 cm³ in size was placed into 1.5 ml centrifuge tube, 200 ul of lysis buffer (same as Example 5) was added, the tissue piece was crushed with a tip, then the mixture was shaken at room temperature for 10 min, then centrifuged at 4° C., and 15000 rpm for 20 min, the supernatant was taken to give a lysate supernatant. The following operation was the same as Example 5. The results showed that 18 cases of lung cancer had Ct values (between 18.11 and 23.23) significantly smaller than the Ct values of the lysate of the control (>30), they were determined as positive for hTERT mRNA, and the detection rate was 90%.

Example 7: Detection the Expression of Human XRCC6 Gene by WFTR-PCR

For the sequences of probe and primer, please refer to the section of Summary, and the preparation of anchor PCR tube, RE/PCR reaction solution were the same as Example 1. The preparation of lysate supernatant of the cell sample, negative control 1 and negative control 2 were the same as Example 1, and the PstI in RE/PCR reaction solution of Example 1 was replaced with EcoRI. The result was as follows:

| Sample Group | Ct-cell | Ct-control 1 | Ct-control 2 |
|---|---|---|---|
| 1 | 28.47 | 31.55 | 31.36 |
| 2 | 28.31 | 31.63 | 31.52 |
| 3 | 28.60 | 31.42 | 31.35 |
| 4 | 28.72 | 31.39 | 31.14 |
| 5 | 28.57 | 31.71 | 31.27 |
| 6 | 28.81 | 31.66 | 31.44 |

Ct value of the cell sample was 28.58+/−0.18; Ct value of negative control 1, i.e. lysate, was 31.56+/−0.13; Ct value of negative control 2, i.e. E. coli lysate supernatant, was 31.35+/−0.13. Ct of the cell sample was significantly smaller than that of negative control 1 or negative control 2 (significantly was defined as the absolute value of difference was ≥1), indicating that WFTR-PCR can detect XRCC6 mRNA of the cell sample; Ct value of negative control 2 was slightly smaller than that of negative control 1, but the absolute value of difference was smaller than 1, which was within the negative fluctuation range.

Example 8: Detection of hTERT mRNA in Human Lung Cancer Cell Strain H1299

For the sequences of probe and primer, please refer to the section of Summary, and the preparation of anchor PCR tube, RE/PCR reaction solution were the same as Example 1. BamHI was used for RE. Human lung cancer cell strain H1299 was incubated in a 24-well plate, the number was from 1 to 10⁶ cells/well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, and the PstI in RE/PCR reaction solution of Example 1 was replaced with BamHI. The result was as follows:

| Sample Group | Ct-1 | Ct-2 | Ct-Average | Result Determination |
|---|---|---|---|---|
| 1 cell | 30.72 | 30.58 | 30.65 | negative |
| 10 cells | 27.51 | 27.63 | 27.57 | positive |
| 100 cells | 23.48 | 23.36 | 23.42 | positive |
| 1000 cells | 20.34 | 20.46 | 20.40 | positive |
| $10^5$ cells | 16.79 | 16.71 | 16.75 | positive |
| $10^6$ cells | 12.51 | 12.83 | 12.67 | positive |
| Negative Control 1 | 31.49 | 31.65 | 31.57 | negative |
| Negative Control 2 | 31.35 | 31.21 | 31.28 | negative |

It can be seen that using the WFTR-PCR process of the present Example, the expression of hTERT mRNA in the 10 to $10^6$ lung cancer A549 cells can be detected, and the detection result is related with the number of cells, wherein the more the cells are, the smaller the Ct value is.

Example 9: Detection of hTERT mRNA in Human Skin Cancer Cell Strain A431

For probe and primer sequences, please see the section of Summary. The preparation of anchor PCR tube, RE/PCR reaction solution were the same as Example 1. BamHI was used for RE. Human skin cancer cell strain A431 was incubated in a 24-well plate, the number was from 1 to $10^6$ cells/well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, and the PstI in RE/PCR reaction solution of Example 1 was replaced with BamHI. The result was as follows:

| Sample Group | Ct-1 | Ct-2 | Ct-Average | Result Determination |
|---|---|---|---|---|
| 1 cell | 31.28 | 31.44 | 31.36 | negative |
| 10 cells | 29.29 | 29.43 | 29.36 | positive |
| 100 cells | 25.68 | 25.44 | 25.56 | positive |
| 1000 cells | 22.23 | 22.38 | 22.31 | positive |
| $10^5$ cells | 18.41 | 18.34 | 18.38 | positive |
| $10^6$ cells | 14.79 | 14.93 | 14.86 | positive |
| Negative Control 1 | 31.67 | 31.55 | 31.61 | negative |
| Negative Control 2 | 31.37 | 31.45 | 31.41 | negative |

It can be seen that using the WFTR-PCR process of the present Example, the expression of hTERT mRNA in the 10 to $10^6$ skin cancer A431 cells can be detected, and the detection result is related with the number of cells, wherein the more the cells are, the smaller the Ct value is.

Example 10: SYBR Green I Dye being Replaced by TaqMan Probe, which has No Influence on the Test Effect of WFTR-PCR For probe and primer sequences please refer to the section of Summary, and the preparation of anchor PCR tube, and RE/PCR reaction solution were the same as Example 1. BamHI was used for RE. Cell strain A549 cell of human lung cancer was cultured in a 24-well plate, and the number is 1 to $10^6$ cells in each well. Culture medium was extracted and removed after overnight culturing. And 200 ul of lysis buffer was added into each well (the concentrations of the template probe B and complementary probe C in the lysis buffer were both 0.1 nmol/L), pipetted repeatedly, then the mixture was transferred to a 1.5 ml centrifuge tube, vibrated at room temperature for 10 minutes and centrifuged at 15000 rpm, and at 4° C. for 20 minutes, the supernatant was taken to give cell lysate supernatant. For the composition of lysis buffer please refer to the above description. The following procedure, negative control 1, and negative control were the same as Example 1, and the PstI in RE/PCR reaction solution of Example 1 was replaced with BamHI, and the SYBR green I of Example 1 was replaced with 0.5 umol/L of TaqMan probe. The result was as follows:

| Sample Group | Ct-1 | Ct-2 | Ct-Average | Result Determination |
| --- | --- | --- | --- | --- |
| 1 cell | 33.81 | 33.77 | 33.79 | negative |
| 10 cells | 30.22 | 30.46 | 30.34 | positive |
| 100 cells | 27.65 | 27.52 | 27.59 | positive |
| 1000 cells | 23.74 | 23.83 | 23.79 | positive |
| $10^5$ cells | 19.56 | 19.72 | 19.64 | positive |
| $10^6$ cells | 16.49 | 16.58 | 16.54 | positive |
| Negative Control 1 | 34.15 | 34.37 | 34.26 | negative |
| Negative Control 2 | 33.95 | 34.07 | 34.01 | negative |

It can be seen that using the WFTR-PCR process with TaqMan probe, the expression of hTERT mRNA in 10 to $10^6$ lung cancer A549 cells can also be detected, and the detection result is related with the number of cells, wherein the more the cells are, the smaller the Ct value is.

Example 11: Detection of GUSB mRNA in Human Skin Cancer Cell Strain A431

For probe and primer sequences, please see the section of Summary. The preparation of anchor PCR tube, RE/PCR reaction solution were the same as Example 1. BamHI was used for RE. Human skin cancer cell strain A431 was incubated in a 24-well plate, the number was from 1 to $10^6$ cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, the PstI in RE/PCR reaction solution of Example 1 was replaced with BamHI, and the SYBR green I of Example 1 was replaced with TaqMan probe. The result was as follows:

| Sample Group | Ct-1 | Ct-2 | Ct-Average | Result Determination |
| --- | --- | --- | --- | --- |
| 1000 cells | 22.47 | 22.39 | 22.43 | positive |
| Negative Control 1 | 33.55 | 33.69 | 33.62 | negative |
| Negative Control 2 | 33.49 | 33.31 | 33.40 | negative |

It can be seen that using the WFTR-PCR process of this Example, the expression of GUSB mRNA in 1000 skin cancer A549 cells can be detected.

Example 12: Detection of BCl-2 mRNA in Human Skin Cancer Cell Strain A431

For probe and primer sequences, please see the section of Summary. The preparation of anchor PCR tube, RE/PCR reaction solution were the same as Example 1. PstI was used for RE. Human skin cancer cell strain A431 was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1. The result was as follows:

| Sample Group | Ct-1 | Ct-2 | Ct-Average | Result Determination |
| --- | --- | --- | --- | --- |
| 1000 cells | 19.77 | 19.58 | 19.68 | positive |
| Negative Control 1 | 31.66 | 31.43 | 31.55 | negative |
| Negative Control 2 | 31.37 | 31.22 | 31.30 | negative |

It can be seen that using the WFTR-PCR process of this Example, the expression of Bcl-2 mRNA can be detected in 1000 skin cancer A431 cells.

Example 13: Detection of PAR-2 mRNA in Human Skin Cancer Cell Strain A431

For probe and primer sequences, please see the section of Summary. The preparation of anchor PCR tube, RE/PCR reaction solution were the same as Example 1. PstI was used for RE. Human skin cancer cell strain A431 was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1. The result was as follows:

| Sample Group | Ct-1 | Ct-2 | Ct-Average | Result Determination |
|---|---|---|---|---|
| 1000 cells | 23.15 | 23.28 | 23.22 | positive |
| Negative Control 1 | 31.81 | 31.62 | 31.72 | negative |
| Negative Control 2 | 31.24 | 31.19 | 31.22 | negative |

It can be seen that using the WFTR-PCR process of this Example, the expression of PAR-2 mRNA can be detected in 1000 skin cancer A431 cells.

Example 14: Detection of RPLP0 mRNA in Human Skin Cancer Cell Strain A431

For probe and primer sequences, please see the section of Summary. The preparation of anchor PCR tube, RE/PCR reaction solution were the same as Example 1. PstI was used for RE. Human skin cancer cell strain A431 was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1. The result was as follows:

| Sample Group | Ct-1 | Ct-2 | Ct-Average | Result Determination |
|---|---|---|---|---|
| 1000 cells | 17.59 | 17.82 | 17.71 | positive |
| Negative Control 1 | 31.51 | 31.66 | 31.59 | negative |
| Negative Control 2 | 31.27 | 31.38 | 31.33 | negative |

It can be seen that using the WFTR-PCR process of this Example, the expression of RPLP0 mRNA can be detected in 1000 skin cancer A431 cells.

Example 15: Detection of GAPDH mRNA in Human Skin Cancer Cell Strain A431

For probe and primer sequences, please see the section of Summary. The preparation of anchor PCR tube, RE/PCR reaction solution were the same as Example 1. HindIII was used for RE. Human skin cancer cell strain A431 was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, but only replacing PstI with HindIII. The result was as follows:

| Sample Group | Ct-1 | Ct-2 | Ct-Average | Result Determination |
|---|---|---|---|---|
| 1000 cells | 18.29 | 18.41 | 18.35 | positive |
| Negative Control 1 | 31.72 | 31.57 | 31.65 | negative |
| Negative Control 2 | 31.37 | 31.20 | 31.29 | negative |

It can be seen that using the WFTR-PCR process of this Example, the expression of GAPDH mRNA can be detected in 1000 skin cancer A431 cells.

Example 16: Detection of ZO1 mRNA in Human Skin Cancer Cell Strain A431

For probe and primer sequences, please see the section of Summary. The preparation of anchor PCR tube, RE/PCR reaction solution were the same as Example 1. BamHI was used for RE. Human skin cancer cell strain A431 was incubated in a 24-well plate, the density of the cells were 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, the PstI in RE/PCR reaction solution of Example 1 was replaced with BamHI. The result was as follows:

| Sample Group | Ct-1 | Ct-2 | Ct-Average | Result Determination |
|---|---|---|---|---|
| 1000 cells | 21.37 | 21.18 | 21.28 | positive |
| Negative Control 1 | 31.43 | 31.62 | 31.53 | negative |
| Negative Control 2 | 31.29 | 31.13 | 31.21 | negative |

It can be seen that using the WFTR-PCR process of this Example, the expression of ZO1 mRNA can be detected in 1000 skin cancer A431 cells.

Example 17: Detection of hTERC mRNA in Human Skin Cancer Cell Strain A431

For probe and primer sequences, please see the section of Summary. The preparation of anchor PCR tube, RE/PCR reaction solution were the same as Example 1. AvaI was used for RE. Human skin cancer cell strain A431 was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, but only replacing PstI with AvaI. The result was as follows:

| Sample Group | Ct-1 | Ct-2 | Ct-Average | Result Determination |
|---|---|---|---|---|
| 1000 cells | 24.72 | 24.63 | 24.68 | positive |
| Negative Control 1 | 31.69 | 31.53 | 31.61 | negative |
| Negative Control 2 | 31.22 | 31.34 | 31.28 | negative |

It can be seen that using the WFTR-PCR process of this Example, the expression of hTERC mRNA can be detected in 1000 skin cancer A431 cells.

Example 18: Detection of b-Actin mRNA in NIH3T3 Cell of Mouse Fibroblast Tumor For probe and primer sequences, please see the section of Summary. The preparation of anchor PCR tube, RE/PCR reaction solution were the same as Example 1. AvaI was used for RE. Mouse fibroblast tumor NIH3T3 cell was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, but only replacing PstI with AvaI. The result was as follows:

| Sample Group | Ct-1 | Ct-2 | Ct-Average | Result Determination |
|---|---|---|---|---|
| 1000 cells | 18.89 | 18.75 | 18.82 | positive |
| Negative Control 1 | 31.57 | 31.74 | 31.67 | negative |
| Negative Control 2 | 31.41 | 31.27 | 31.34 | negative |

It can be seen that using the WFTR-PCR process of this Example, the expression of b-actin mRNA can be detected in 1000 mouse fibroblast tumor NIH3T3 cells.

Example 19: Detection of Col4a1 mRNA in NIH3T3 Cell of Mouse Fibroblast Tumor For probe and primer sequences, please see the section of Summary. The preparation of anchor PCR tube, RE/PCR reaction solution were the same as Example 1. BamHI was used for RE. Mouse fibroblast tumor NIH3T3 cell was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, but only replacing PstI with BamHI. The result was as follows:

| Sample Group | Ct-1 | Ct-2 | Ct-Average | Result Determination |
|---|---|---|---|---|
| 1000 cells | 28.19 | 28.88 | 28.04 | positive |
| Negative Control 1 | 31.77 | 31.62 | 31.70 | negative |
| Negative Control 2 | 31.23 | 31.40 | 31.32 | negative |

It can be seen that using the WFTR-PCR process of this Example, the expression of Col4a1 mRNA can be detected in 1000 mouse fibroblast tumor NIH3T3 cells.

Example 20: Detection of Wrn mRNA in NIH3T3 Cell of Mouse Fibroblast Tumor

For probe and primer sequences, please see the section of Summary. The preparation of anchor PCR tube, RE/PCR reaction solution were the same as Example 1. BamHI was used for RE. Mouse fibroblast tumor NIH3T3 cell was incubated in a 24-well plate, the density was 1000 cells per well. After incubation overnight, the culture medium was removed, and 200 ul of lysis buffer was added (concentrations of template probe B and complementary probe C in the lysis buffer were both 0.1 nmol/L) into each well, pipetted repeatedly and transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1, negative control 2 were the same as Example 1, but only replacing PstI with BamHI. The result was as follows:

| Sample Group | Ct-1 | Ct-2 | Ct-Average | Result Determination |
|---|---|---|---|---|
| 1000 cells | 27.76 | 27.59 | 27.68 | positive |
| Negative Control 1 | 31.47 | 31.58 | 31.53 | negative |
| Negative Control 2 | 31.44 | 31.29 | 31.37 | negative |

It can be seen that using the WFTR-PCR process of this Example, the expression of Wrn mRNA can be detected in 1000 mouse fibroblast tumor NIH3T3 cells.

Example 21: Detection of Expression of Ampicillin Resistance Gene (Amp$^r$) in *Escherichia coli*

For probe and primer sequences, please see the section of Summary. The preparation of anchor PCR tube, RE/PCR reaction solution were the same as Example 1. MboI was used for RE. 1 ml of LB culture medium containing 50 ug/ml of ampicillin was used for incubating *Escherichia coli* DH5a transferred with pcDNA3.1 plasmid, the *E. coli* was cultured at the temperature of 37° C. until the OD600 of the medium=1.0, and the bacteria precipitate was collected by centrifugation. 200 ul of lysis buffer was added (concentrations of template probe B and complementary probe C in the lysis buffer were both 0.1 nmol/L) to the bacteria precipitate, pipetted repeatedly then transferred to a 1.5 ml centrifuge tube, shaken at room temperature for 10 min, centrifuged at 4° C. and 15000 rpm for 20 min, the supernatant was taken to obtain the cell lysate supernatant. The composition of the lysis buffer was the same as the above said description. The following procedure and negative control 1 were the same as Example 1, and negative control 2 was the lysate supernatant of A431 cells prepared in Example 1. For RE/PCR PstI was replaced with MboI. The result was as follows:

| Sample Group | Ct-1 | Ct-2 | Ct-Average | Result Determination |
|---|---|---|---|---|
| E. coli | 15.24 | 15.48 | 15.36 | positive |
| Negative Control 1 | 31.41 | 31.56 | 31.49 | negative |
| Negative Control 2 | 31.39 | 31.27 | 31.33 | negative |

It can be seen that using the WFTR-PCR process of this Example, the expression of Amp$^r$ gene can be detected in the E. coli DH5a transferred with pcDNA3.1.

What is claimed is:

1. A washing-free template-ready PCR process for detecting RNA in a sample, comprising:
    (1) synthesizing a probe A that is a single-stranded oligonucleotide DNA having a length of 25 to 50 mer complementary to a section of a target RNA sequence, and anchoring the probe A onto a PCR tube to obtain an anchored PCR tube, wherein the probe A has a GC content of 40% to 60% and a melting temperature of 75 to 85° C.;
    (2) synthesizing a template probe B that is a single-stranded oligonucleotide DNA having a length of 70 to 100 mer that is partially complementary to another section of the target RNA sequence containing a restriction endonuclease recognition site, wherein in a middle part of the template probe B is a sequence of 25 to 50 mer completely complementary to a region containing the restriction endonuclease recognition site of the target RNA sequence, at both ends of the template probe B are PCR primer sequences having a length of 20 to 30 mer, respectively, the template probe B has a GC content of 40% to 60% and a melting temperature of from 75 to 85° C., and the template probe B has no overlap with the probe A at a region binding to the target RNA sequence;
    (3) synthesizing a complementary probe C that is a single-stranded oligonucleotide DNA having a length of 15 to 30 mer, wherein the complementary probe C is completely complementary to a part of the sequence containing the restriction endonuclease recognition site of the template probe B, and the complementary probe C has a melting temperature of 50 to 60° C.;
    (4) mixing the sample with the template probe B, the complementary probe C and a lysis buffer to obtain a mixture, the obtained mixture being centrifuged to obtain a lysate supernatant; and
    (5) transferring the lysate supernatant into the anchored PCR tube to perform hybridization, removing liquid in the anchored PCR tube, adding a restriction endonuclease and PCR reaction solution into the anchored PCR tube to perform restriction endonuclease digestion and PCR amplification to obtain an amplified product, the amplified product being subjected to fluorescent quantitative analysis.

2. The washing-free template-ready PCR process of claim 1, wherein the lysis buffer in the step (4) comprises: 4.0 mol/L of guanidine isothiocyanate, 350 mmol/L of NaCl, 1% of Triton X-100, 10 mmol/L of 2-mercaptoethanol, 0.1 mg/ml of salmon sperm DNA, and 10 mmol/L of Tris-HCl at pH 7.5.

3. The washing-free template-ready PCR process of claim 1, wherein the restriction endonuclease and PCR reaction solution of the step (5) comprises: 50 mmol/L of KCl, 1.5 mmol/L of $MgCl_2$, 0.2 mmol/L of dNTP, 0.05% of Tween20, 0.4×SYBR Green I, 0.5 U/20 uL of Taq enzyme, 4 U/20 uL of restriction endonuclease, 0.2 umol/L of PCR primer, and 10 mmol/L of Tris-HCl at pH 9.0.

4. The washing-free template-ready PCR process of claim 1, wherein the restriction endonuclease is selected from the group consisting of PstI, BamHI, EcoRI, HindIII, AvaI, and MboI.

* * * * *